United States Patent
Lia et al.

(10) Patent No.: US 11,896,356 B2
(45) Date of Patent: Feb. 13, 2024

(54) REVERSIBLE BLOOD PRESSURE MEASUREMENT CUFF AND MANUFACTURING METHOD THEREFOR

(71) Applicant: Welch Allyn, Inc., Skaneateles Falls, NY (US)

(72) Inventors: Raymond A Lia, Skaneateles Falls, NY (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 504 days.

(21) Appl. No.: 17/079,091

(22) Filed: Oct. 23, 2020

(65) Prior Publication Data
US 2021/0121086 A1    Apr. 29, 2021

Related U.S. Application Data

(60) Provisional application No. 62/943,474, filed on Dec. 4, 2019, provisional application No. 62/924,923, filed on Oct. 23, 2019.

(51) Int. Cl.
*A61B 5/022*    (2006.01)

(52) U.S. Cl.
CPC ................. *A61B 5/02233* (2013.01)

(58) Field of Classification Search
CPC .............................. A61B 5/02; A61B 5/02233
See application file for complete search history.

(56) References Cited

U.S. PATENT DOCUMENTS

| | | | | |
|---|---|---|---|---|
| 5,069,219 | A * | 12/1991 | Knoblich | A61B 5/02233 600/492 |
| 5,413,582 | A | 5/1995 | Eaton | |
| 2009/0062668 | A1* | 3/2009 | Todokoro | A61B 5/02233 600/499 |
| 2010/0298724 | A1* | 11/2010 | Vivenzio | A61B 5/02233 600/490 |
| 2013/0053708 | A1 | 2/2013 | Quinn et al. | |
| 2015/0216430 | A1* | 8/2015 | Quinn | A61B 5/02233 600/499 |
| 2020/0330037 | A1* | 10/2020 | Al-Ali | F04B 53/001 |

FOREIGN PATENT DOCUMENTS

WO    WO2016033264 A1    3/2016

OTHER PUBLICATIONS

Copy of the Extended European Search Report dated Mar. 24, 2021 for European Patent Application No. 1 20203636.4, 7 pages.

\* cited by examiner

*Primary Examiner* — Devin B Henson
*Assistant Examiner* — Jonathan M Haney
(74) *Attorney, Agent, or Firm* — Lee & Hayes, P.C.

(57) ABSTRACT

A blood pressure cuff includes a smaller patient bladder extending laterally across the cuff and longitudinally along a minor portion of second and fourth perimeter segments of the cuff. The cuff also includes a larger patient bladder extending laterally across the cuff and longitudinally along a major portion of the second and fourth perimeter segments of the cuff. The smaller patient bladder and the larger patient bladder are fluidically isolated from each other. A small patient port projects through the smaller patient bladder on a first side of the cuff. A large patient port projects through the larger patient bladder on a second side of the cuff which is transversely opposite the first side.

20 Claims, 12 Drawing Sheets

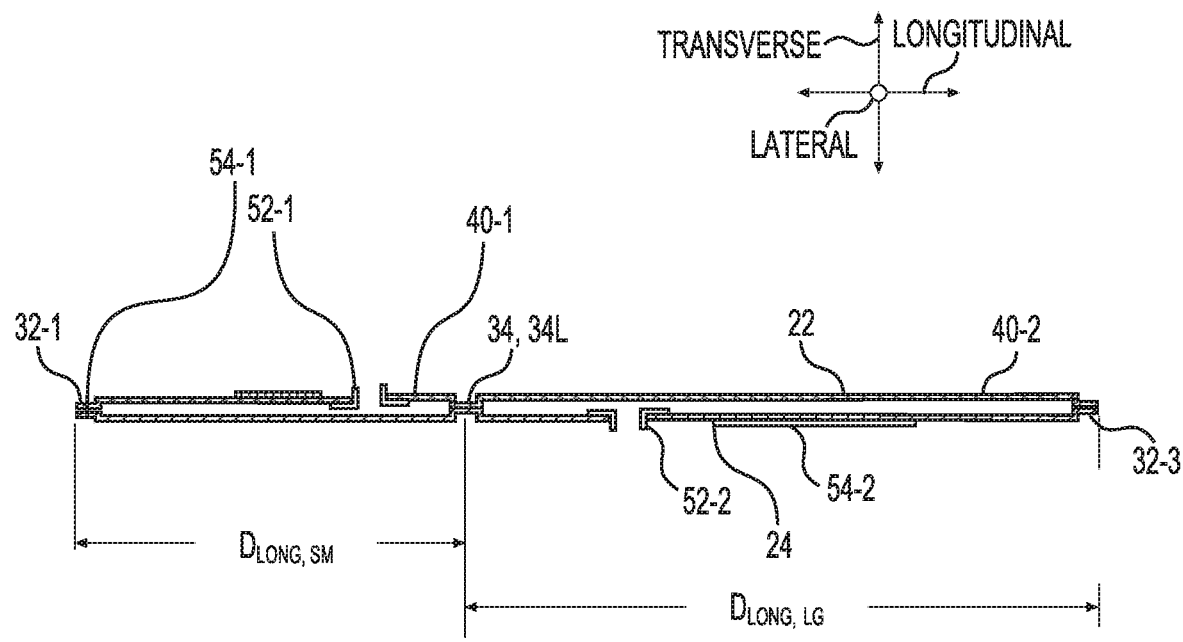
FIG. 2
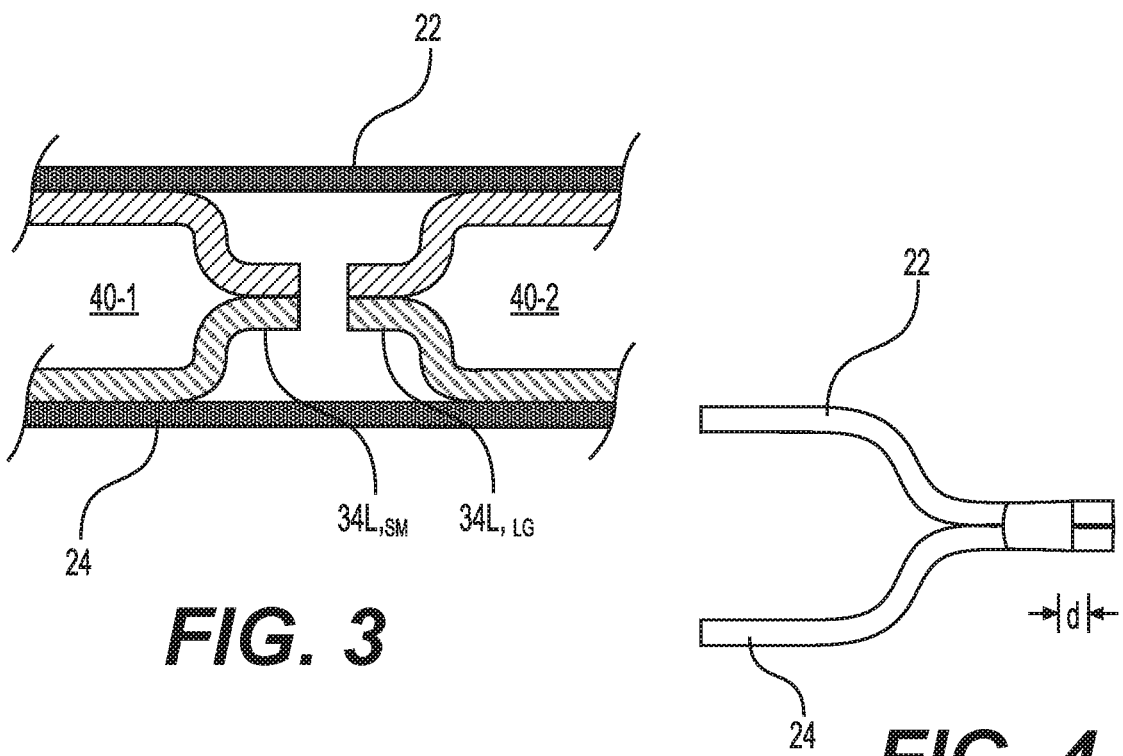
FIG. 3     FIG. 4

REVERSIBLE BLOOD PRESSURE MEASUREMENT CUFF AND MANUFACTURING METHOD THEREFOR

CROSS REFERENCE TO RELATED APPLICATIONS

The present application claims priority to and the benefit of U.S. Provisional Patent Application No. 62/924,923, titled "Reversible Blood Pressure Measurement Cuff," filed Oct. 23, 2019, which is incorporated herein by reference in its entirety, and U.S. Provisional Patent Application No. 62/943,474, titled "Reversible Blood Pressure Measurement Cuff and Manufacturing Method Therefor," filed Dec. 4, 2019, which is incorporated herein by reference in its entirety.

TECHNICAL FIELD

The subject matter described herein relates to blood pressure measurement cuffs and particularly to a cuff which will provide an accurate blood pressure reading for a wide range of patient arm sizes.

BACKGROUND

In the medical arts a patient's blood pressure is often measured with a blood pressure measurement apparatus that includes a cuff having an air-pressurizable bladder, devices to inflate (pressurize) and deflate (depressurize) the bladder with ambient air, and a gauge for displaying the air pressure within the bladder. In practice, a caregiver wraps the cuff around a patient's upper arm, and inflates the bladder sufficiently to collapse the brachial artery and stop blood flow therethrough. The caregiver then slowly deflates the bladder and notes the pressure indicated on the gauge at cardiac systole (systolic blood pressure) and diastole (diastolic blood pressure) as blood flow through the artery re-establishes itself.

Blood pressure cuffs are available in various sizes to accommodate different patient arm sizes. Use of a cuff whose size is mismatched to the length and circumference of the patient's upper arm may yield an inaccurate blood pressure reading. Therefore, patient care facilities need to bear the expense of stocking several different cuff sizes to cover the size range of patients expected to be treated. However even if cuffs of different sizes are available in a facility, a caregiver with a high workload may make do with a cuff that happens to be nearby rather than take time to seek out a differently sized cuff more appropriate for the size of the patient.

It is, therefore, desirable to provide a blood pressure cuff which is accurate but which also accommodates patient size ranges which presently must be accommodated by two or more cuffs.

SUMMARY

A blood pressure cuff includes a smaller patient bladder extending laterally across the cuff and longitudinally along a minor portion of second and fourth perimeter segments of the cuff. The cuff also includes a larger patient bladder extending laterally across the cuff and longitudinally along a major portion of the second and fourth perimeter segments of the cuff. The smaller patient bladder and the larger patient bladder are fluidically isolated from each other. A small patient port projects through the smaller patient bladder on a first side of the cuff. A large patient port projects through the larger patient bladder on a second side of the cuff which is transversely opposite the first side.

BRIEF DESCRIPTION OF THE DRAWINGS

The foregoing and other features of the various embodiments of the blood pressure cuff described herein will become more apparent from the following detailed description and the accompanying drawings in which:

FIG. 2 is a cross sectional side elevation view of the assembled cuff taken in the direction 2-2 of FIG. 1A or 2-2 of FIG. 1B.

FIG. 3 is a cross sectional side elevation view near the cuff lateral centerline showing an alternative construction.

FIG. 4 is a magnified cross-sectional side elevation view showing one end of the cuff of FIG. 2.

DETAILED DESCRIPTION

Figure 1A:
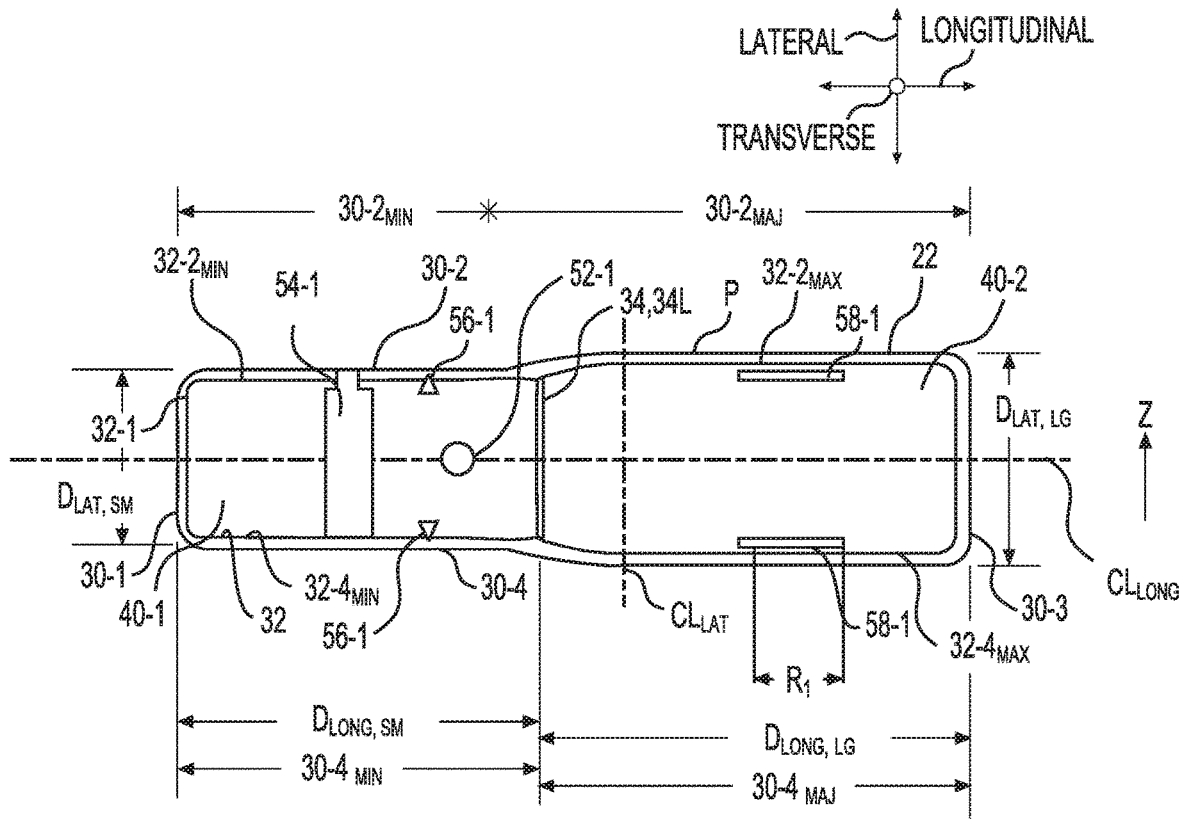
FIG. 1A is a plan view in direction 1A-1A of FIG. 2 of an embodiment of a blood pressure cuff as described herein showing the first or small patient side of the cuff.

The present invention may comprise one or more of the features recited in the appended claims and/or one or more of the following features or combinations thereof. Additionally, in this specification and drawings, features similar to or the same as features already described may be identified by reference characters or numerals which are the same as or similar to those previously used. Similar elements may be identified by a common reference character or numeral, with suffixes being used to refer to specific occurrences of the element.

Figure 1B:
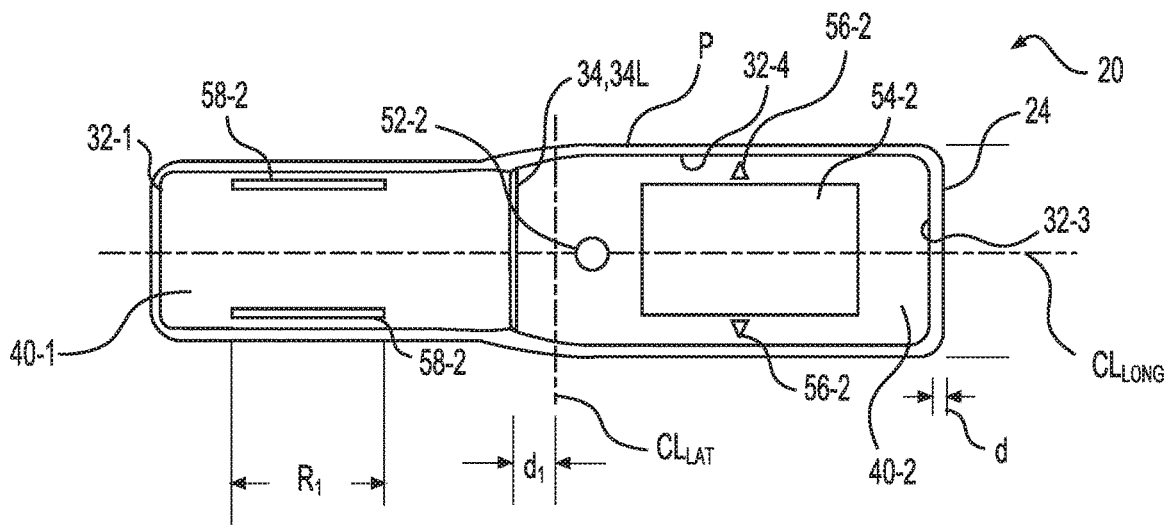
FIG. 1B is a plan view in direction 1B-1B of FIG. 2 of the second or large patient side of the cuff.
Figure 5:
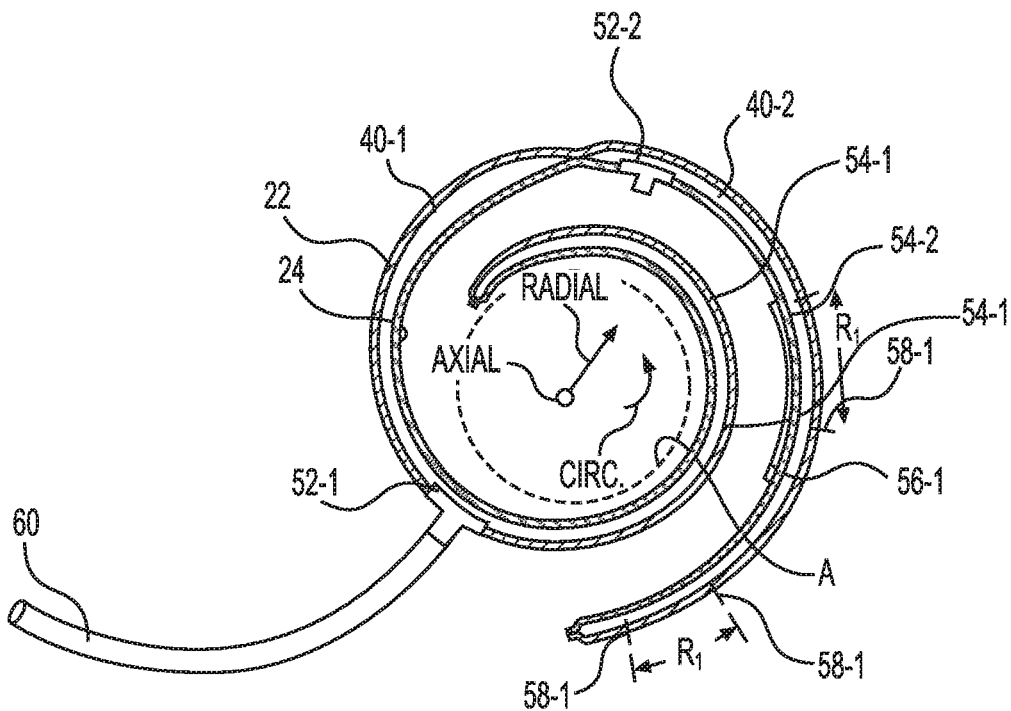
FIG. 5 is a view of the cuff of FIG. 2 wrapped around the arm of a small patient and secured in a sleeve-like configuration by first and second closure elements which are engaged with each other.
Figure 6:
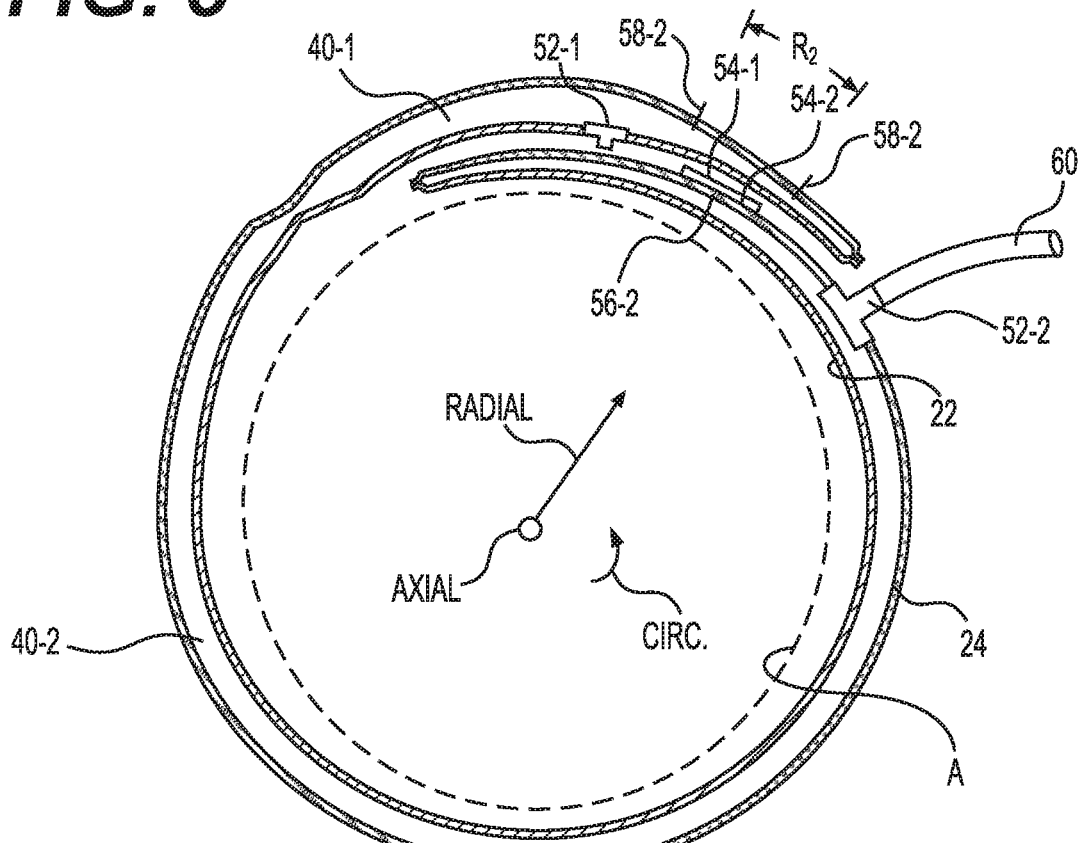
FIG. 6 is a view of the cuff of FIG. 2 wrapped around the arm of a large patient and secured in a sleeve-like configuration by first and second closure elements which are engaged with each other.

FIGS. 1A, 1B and 2-6 show a blood pressure cuff 20 which is a component of a blood pressure measuring apparatus. Cuff 20 extends longitudinally, laterally, and transversely as indicated by the axes included on the illustration. When wrapped around a patient's limb in order to take a blood pressure measurement as seen in FIGS. 5-6 it may be more natural to refer to the longitudinal, lateral, and transverse directions as circumferential, limbwise or axial, and radial directions respectively. Nevertheless, the directional terms from either set of coordinates may be used irrespective of whether the cuff is laid flat as in FIGS. 1A, 1B and 2 or wrapped as in FIGS. 5-6. The transverse (radial) dimension of the cuff or its components may be referred to as "thickness". FIGS. 1A and 1B also show a longitudinally extending centerline $CL_{LONG}$, and a laterally extending centerline $CL_{LAT}$.

The cuff has a first side 22 and a second side 24 transversely opposite the first side 24. As will be explained in more detail below, the cuff is reversible in that it may be wrapped as in FIG. 5 so that second side 24 is against the patient's arm A (dashed lines) and first side 22 is exposed in order to take a blood pressure reading from a smaller patient. Or, the cuff may be wrapped as in FIG. 6 so that first side 22 is against the patient's arm A and second side 24 is exposed in order to take a blood pressure reading from a larger patient. Accordingly, first side 22 may be referred to as the small patient side since it is the side which is visible when the cuff is used on a smaller patient. Similarly, second side 24 may be referred to as the large patient side since it is the side which is visible when the cuff is used on a larger patient.

In some embodiments, the first side 22 and the second side 24 may be sealed to each other at a cuff perimeter P comprised of laterally extending, longitudinally spaced apart first perimeter segment 30-1 and third perimeter segment 30-3 and longitudinally extending, laterally spaced apart second perimeter segment 30-2 and fourth perimeter segment 30-4. A first sealed perimeter segment 32-1 may be associated with the first perimeter segment 30-1, a second sealed perimeter segment 32-2 may be associated with the second perimeter segment 30-2, a third sealed perimeter segment 32-3 may be associated with the third perimeter segment 30-3, and a fourth sealed perimeter segment 32-4 may be associated with the fourth perimeter segment 30-4. The sealed perimeter segments may be referred to as perimeter segment seals 32-1, 32-2, 32-3, 32-4, each of which corresponds substantially to perimeter segments 30-1, 30-2, 30-3, 30-4. The seal around the entire perimeter, i.e. the combination of seals 32-1 through 32-4 along segments 30-1 through 30-4 may be referred to as a perimeter seal 32P. As used herein, "perimeter" need not be at the actual edges of the cuff, but may be offset slightly from the actual edges by a distance d (seen best in FIG. 4). Moreover, the word "segments" may be used as a convenience to refer to different portions of a continuous seal.

In some additional embodiments, the first side 22 and the second side 24 of the cuff may be sealed to each other at a nonperimetric terminus 34 which extends laterally across the cuff. The sealed terminus may be referred to as a lateral seal 34L. For example, as illustrated by FIGS. 1A and 1B, the lateral seal 34L may be common to a smaller patient bladder 40-1 and a larger patient bladder 40-2. In an additional example, FIG. 3 shows a variant in which the smaller patient bladder 40-1 and the larger patient bladder 40-2 each have a dedicated lateral seal $34L_{SM}$, $34L_{LG}$. The terminus 34 and/or the lateral seal 34L may be longitudinally offset from cuff lateral centerline $CL_{LAT}$ by distance di, thereby defining a second perimeter minor portion $30\text{-}2_{MIN}$ and a second perimeter major portion $30\text{-}2_{MAJ}$ of second perimeter segment 30-2, and a fourth perimeter minor portion $30\text{-}4_{MIN}$ and a fourth perimeter major portion $30\text{-}4_{MAJ}$ of the fourth perimeter segment 30-4. The second perimeter seal segment 32-2 and the fourth perimeter seal segment 32-4 can also be thought of as having minor and major portions $32\text{-}2_{MIN}$, $32\text{-}2_{MAJ}$, $32\text{-}4_{MIN}$, $32\text{-}4_{MAJ}$. The lengths of the second perimeter minor portion $30\text{-}2_{MIN}$ and the fourth perimeter minor portion $30\text{-}4_{MIN}$, and the corresponding seals, can have a first length. Similarly, the lengths of the second perimeter major portion $30\text{-}2_{MAJ}$ and the fourth perimeter major portion $30\text{-}4_{MAJ}$, and the corresponding seals, can have a second length. Alternatively, or in addition, lengths associated with the second perimeter minor portion $30\text{-}2_{MIN}$, the second perimeter major portion $30\text{-}2_{MAJ}$, the fourth perimeter minor portion $30\text{-}4_{MIN}$, and the fourth perimeter major portion $30\text{-}4_{MAJ}$ may vary. In some further examples, the major portions may be longer than the minor portions.

In one embodiment, the first side 22 and the second side 24 can be made of a first material that can be heat welded to itself. In another embodiment, the first side 22 can be made of the first material and the second side 24 can be made a second material, wherein the first material and the second material can be heat welded to each other. It should be noted that suitable heat welding techniques include ultrasonic welding and radio frequency (RF) welding. Additionally, other joinery techniques for making the perimeter seal and transverse seal may be satisfactory. Other materials and compatible joinery techniques may also be satisfactory.

In some embodiments, the first perimeter seal 32-1, the lateral seal 34L, the second perimeter seal minor portion $32\text{-}2_{MIN}$, and the fourth perimeter seal minor portion $32\text{-}4_{MIN}$ may define a smaller patient bladder 40-1 extending laterally across the cuff and longitudinally along the second perimeter minor portion $30\text{-}2_{MIN}$ and the fourth perimeter minor portion $30\text{-}4_{MIN}$. Similarly, the third perimeter seal 32-3, the lateral seal 34L, the second perimeter seal major portion $32\text{-}2_{MAX}$, and the fourth perimeter seal major portion $32\text{-}4_{MAX}$ may define a larger patient bladder 40-2 extending laterally across the cuff and longitudinally along the second perimeter major portion $30\text{-}2_{MAJ}$ and the fourth perimeter major portion $30\text{-}4_{MAJ}$. The smaller patient bladder 40-1 may be smaller than the larger bladder 40-2 and may be inflated to measure blood pressure of a smaller patient. Conversely, bladder 40-2 may be larger than the smaller patient bladder 40-1 and may be inflated to measure blood pressure of a larger patient.

In some examples, the smaller patient bladder 40-1 and the larger patient bladder 40-2 can be fluidically isolated from each other by the lateral seal 34L (or by smaller lateral seal $34L_{SM}$ and larger lateral seal $34L_{LG}$). In other words, the smaller patient bladder 40-1 and the larger patient bladder 40-2 may not be in fluid communication with each other. Fluidic isolation and lack of fluid communication between the bladders means that there is no fluid pathway that connects the bladders to each other without involving the ambient environment. Therefore, ports associated with the smaller patient bladder 40-1 and the larger patient bladder 40-2 may be open to the ambient environment without causing them to be in fluid communication with each other and does not defeat their status as being fluidically isolated from each other.

In some examples, a small patient port 52-1 may project through the smaller patient bladder on the first side 22 (small patient side) of the cuff. Similarly, a large patient port 52-2 may project through the larger patient bladder on the second side 24 (large patient side) of the cuff. Although the small patient port 52-1 and the large patient port 52-2 may be the same physical size as each other, "small" is used to designate port 52-1 because it is the port used for inflation and deflation of the smaller patient bladder 40-1 when the cuff is used for a small size patient. Similarly, port 52-2 is referred to as "large" because it is the port used for inflation and deflation of the larger patient bladder 40-2 when the cuff is used for a large size patient.

As seen best in FIGS. 5 and 6, a tube 60 connects the cuff, by way of small patient port 52-1 and/or large patient port 52-2, to components of a blood pressure measurement apparatus such as a device or devices for inflating and deflating the cuff and a gauge for measuring the air pressure inside the smaller patient bladder 40-1 and/or the larger patient bladder 40-2. The tube 60 can be connected to and disconnected from the small patient port 52-1 and/or the large patient port 52-2 depending on whether the cuff is to be used on a small patient or a large patient.

The cuff also includes a closure assembly which may include a first closure element 54-1 exposed on the first side 22 of the cuff longitudinally outboard of the small patient port 52-1 and a second closure element 54-2 exposed on the second side 24 of the cuff longitudinally outboard of the large patient port 52-2. As used herein, a first feature F1 is more outboard than a second feature F2 if both features are on the same side of centerline $CL_{LAT}$, F1 is further from centerline $CL_{LAT}$, and F2 is closer to centerline $CL_{LAT}$. Additionally, the first closure element 54-1 and the second closure element 54-2 can be adapted to engage each other thereby holding the cuff in a sleeve configuration as seen in, for example, FIGS. 5-6. In at least one embodiment, the first closure element 54-1 can be a hook member of a hook and loop fastener pair, and the second closure element 54-2 can be the loop member of the hook and loop fastener pair. In at least one additional embodiment, there is exactly one (i.e. one and only one) first closure element and exactly one (i.e. one and only one) second closure element.

The smaller patient bladder 40-1 and the larger patient bladder 40-2 may have a longitudinal dimension and a lateral dimension. In at least one embodiment, a first longitudinal dimension $D_{LONG,SM}$ of the smaller patient bladder 40-1 may be shorter than a second longitudinal dimension $D_{LONG,LG}$ of the larger patient bladder 40-2. In at least the embodiment illustrated by FIG. 1, a lateral dimension $D_{LAT,SM}$ of the longitudinally smaller patient bladder 40-1 may be shorter than a second lateral dimension $D_{LAT,LG}$ of the longitudinally larger patient bladder 40-2.

In some examples, thee cuff can include a small patient size marker 56-1 on the first side (small patient side) 22 of the smaller patient bladder 40-1, and a small patient range guide 58-1 on the first side 22 of the larger patient bladder 40-2. As seen in FIG. 5, when the cuff is snugly wrapped around the arm of a small patient, the caregiver may ensure that the small patient size marker 56-1 falls within (matches) the circumferential range $R_1$ of small patient range guide 58-1. (In FIG. 5 marker 56-1 is indicated by a short radial line segment cutting across first side 22, and range guide 58-1 is indicated by a pair of short radial line segments cutting across first side 22.) If the marker and range guide do not match, a different cuff might be required. For example if the cuff is expected to accommodate a patient range from a child to a small adult, and the marker fails to reach the range guide, the caregiver may need to use a different cuff that accommodates a patient range from medium adult to large adult, or may simply need to reverse the polarity of the cuff to the polarity seen in FIG. 6.

In some additional examples, the cuff may include a large patient size marker 56-2 on the second side (large patient side) 24 of the larger patient bladder 40-2, and a large patient range guide 58-2 on the second side 24 of the smaller patient bladder 40-1. As seen in FIG. 6, when the cuff is wrapped around the arm of a large patient, the caregiver may ensure that the large patient size marker 56-2 falls within (matches) the circumferential range $R_2$ of the large patient range guide 58-2. (In FIG. 6 marker 56-2 is indicated by a short radial line segment cutting across second side 24, and range guide 58-2 is indicated by a pair of short radial line segments also cutting across second side 24.) If the marker and range guide do not match, a different cuff might be required. For example if the cuff is expected to accommodate a patient range from a medium adult to a large adult, and the marker extends past the range guide without the cuff fitting snugly, the caregiver may need to use a different cuff that accommodates a patient range from child to small adult, or may simply need to reverse the polarity of the cuff to the polarity seen in FIG. 5.

Figures 7A, 7B:
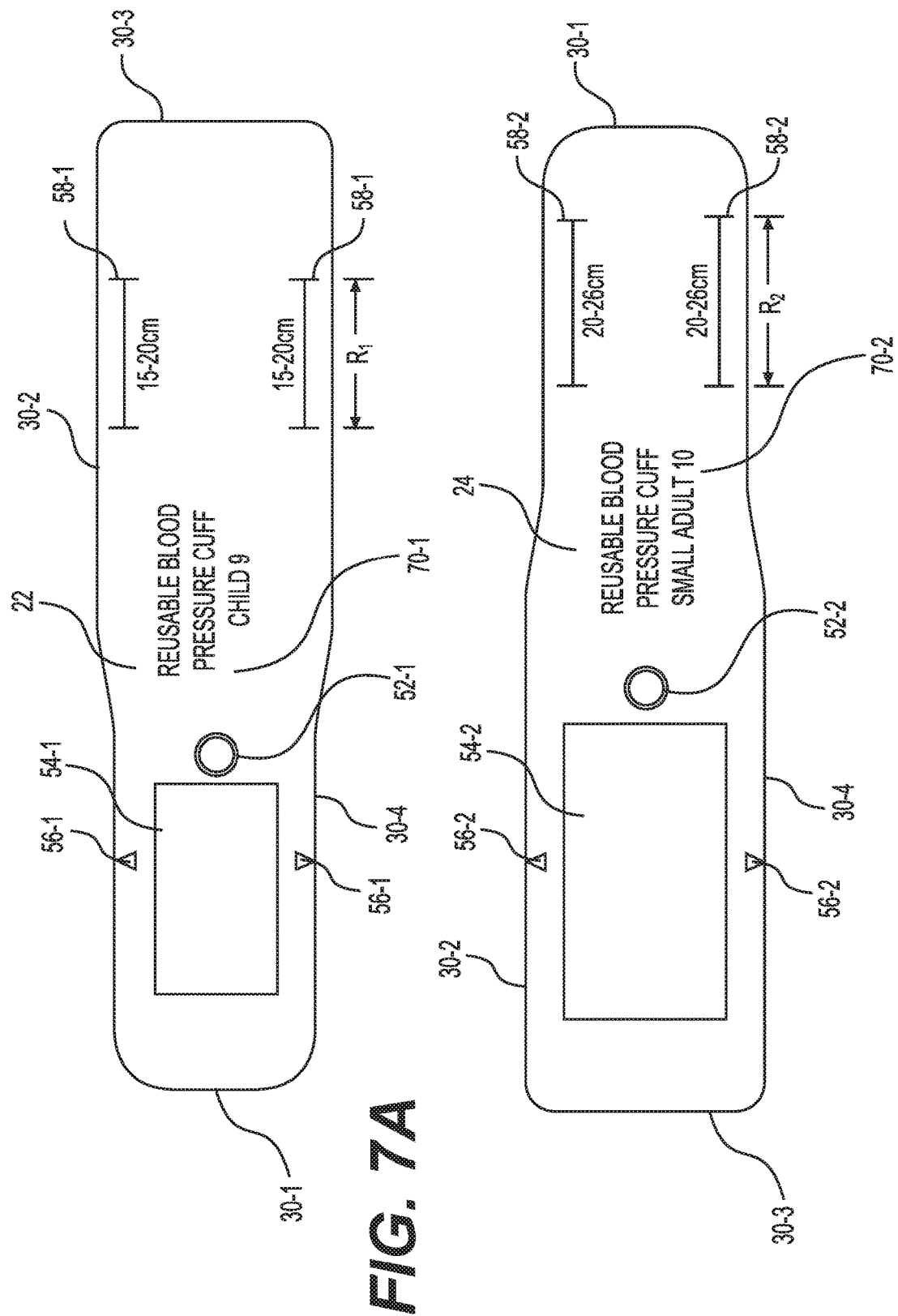
FIG. 7A is a view similar to that of FIG. 1A showing two examples of a polarity indicator.
FIG. 7B is a view similar to that of FIG. 1B showing two examples of a polarity indicator which is complementary to the polarity indicator of FIG. 7A.

Referring additionally to FIGS. 7A-7B, one side (e.g. the first side 22 or small patient side) of the cuff may include a polarity indicator, and the other side (e.g. the second side 24 or large patient side) may include a complementary polarity indicator. The polarity indicator and the complementary polarity indicator may inform the user of the cuff polarity, i.e. whether the cuff is oriented for a small patient or for a large patient.

In some examples, the polarity indicator and the complementary polarity indicator may be a color. In at least one example, the polarity indicator may be a blue coloring of the first side (small patient side) 22 and the complementary polarity indicator is a maroon coloring of the second side (large patient side) 24. In at least one additional example, the polarity indicator and the complementary polarity indicator may be a first label 70-1 and a second label 70-2 that may include symbols, words, size numbers, or some combination thereof. For instance, "label" can mean a separate article which is affixed to the cuff during manufacture, or it can mean symbols which appear directly on the cuff material. In at least one further example, and as illustrated by FIG. 7A, the first label 70-1 "Child 9" may appear on the first side (small patient side) 22 and the second label 70-2 "Small Adult 10" may appear on the second side (large patient side) 24. When "Child 9" is visible to the caregiver, it signifies that the cuff polarity is compatible with a small patient, i.e. a child. When "Small Adult 10" is visible to the caregiver, it signifies that the cuff polarity is compatible with a large patient, i.e. a small adult. Multiple polarity indicators and complementary polarity indicators can be used, for example a combination of color and labeling.

In practice, a caregiver may use whichever side of the cuff is appropriate for the size of the patient. If the patient is small the caregiver may use the cuff as seen in FIG. 5. If the patient is large the caregiver may use the cuff as seen in FIG. 6.

In view of the foregoing, certain additional features of the cuff can now be better appreciated. Longitudinal dimensions $D_{LONG,SM}$, $D_{LONG,LG}$ are such that when the cuff is wrapped around the upper arm of a small patient with the first side 22 contacting the patient, the smaller patient bladder 40-1 may completely encircle an arm of the patient or at least extends circumferentially a first distance sufficient to collapse the brachial artery when inflated and yield an accurate blood pressure measurement. Longitudinal dimensions $D_{LONG,SM}$, $D_{LONG,LG}$ are also sized so that when the cuff is wrapped around the upper arm of a large patient with the second side 24 contacting the patient, the larger patient bladder 40-2 may completely encircle patient's arm or at least extends circumferentially a second distance sufficient to collapse the brachial artery when inflated and yield an accurate blood pressure measurement. Limbwise dimensions $D_{LAT,SM}$ and $D_{LAT,LG}$ are selected to be short enough that the cuff fits on the arm of the patient.

Another feature is the relative longitudinal positioning of a first port 52-1, a second port 52-2, a first closure element 54-1, and a second closure element 54-2 so that when the cuff is in the correct polarity for a given patient and is correctly wrapped around the patient's arm, a working port (the port in communication with the bladder to be inflated) is accessible, and an idle port (the port in communication with the bladder which is not to be inflated) is inaccessible. Whichever bladder is in communication with the working port may be referred to as the working bladder, and whichever bladder is in communication with the idle port may be referred to as the idle bladder. For example, the cuff as seen in FIG. 5 is wrapped around the arm of a small patient. Therefore the first port 52-1 is the working port and is accessible for inflating smaller patient bladder 40-1 and the second port 52-2, which communicates with larger patient bladder 40-2, is the idle port, is inaccessible, and is separated from the patient's arm by the smaller patient bladder. Alternatively, or in addition, an additional example of the cuff, as seen in FIG. 6, can be wrapped around the arm of a large patient. Therefore the second port 52-2 is the working port and is accessible for inflating larger patient bladder 40-2 and the second port 52-1, which communicates with smaller patient bladder 40-1, is the idle port, is inaccessible, and is separated from the patient's arm by the larger patient bladder 40-2. Independent of the cuff configuration, the cuff may be configured such that one port is accessible and that the accessible port is the port in communication with the bladder which should be inflated, can reduce or eliminate any confusion that might arise if both ports were accessible.

The relative longitudinal positioning of the first closure element 54-1, the second closure element 54-2, the first port 52-1, and the second port 52-2 can be configured such that the idle port is radially separated from the patient's arm by the intervening inflated bladder. For example, and as illustrated by FIG. 5, the cuff may be wrapped around the arm of a small patient. Therefore, idle port (e.g., the second port 52-2) can be radially separated from the patient's arm by at least working bladder 40-1, the bladder which is to be inflated. In some additional examples, and as illustrated by FIG. 6, the cuff may be wrapped around the arm of a large patient. Therefore, idle port (e.g., the first port 52-1) can be radially separated from the patient's arm by at least working bladder 40-2, the bladder which is to be inflated. In particular, the cuff may be configured such that the idle port is separated from the arm of the patient and may prevent and/or reduce patient discomfort that might arise if the idle port, which is somewhat rigid, were in contact with the patient's arm.

Continuing to refer to FIGS. 5-6, the relative longitudinal positioning of the closure elements is such that when the cuff is in a correct polarity for a given patient and is correctly wrapped around a limb of the patient, neither closure element is in contact with the patient's limb.

Figure 8:
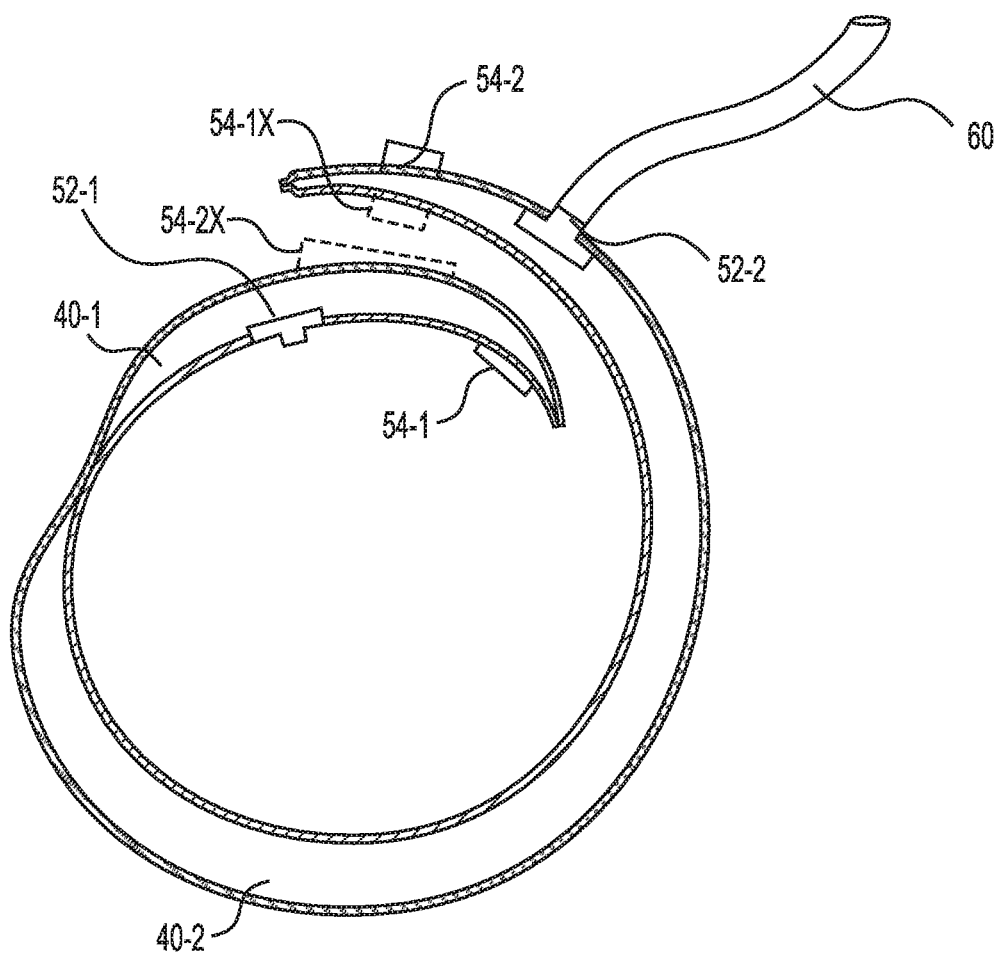
FIG. 8 is a view similar to that of FIG. 6 showing additional closure elements and illustrating a disadvantage of the additional closure elements.

In some embodiments, the first side 22 and the second side 24 may individually include one closure element that is configured to ensure or assists the correct usage of the cuff. For instance, FIG. 8 includes potentially undesirable additional closure elements 54-1X, 54-2X. The presence of the "X" closure elements may invite the caregiver to use those closure elements, instead of the first closure element 54-1 and the second closure element 54-2, causing both the first port 52-1 and the first closure element 54-1 to be in contact with the patient's skin. Such contact may be uncomfortable for the patient and may even break the patient's skin when the larger patient bladder 40-2 is inflated.

Figure 9:
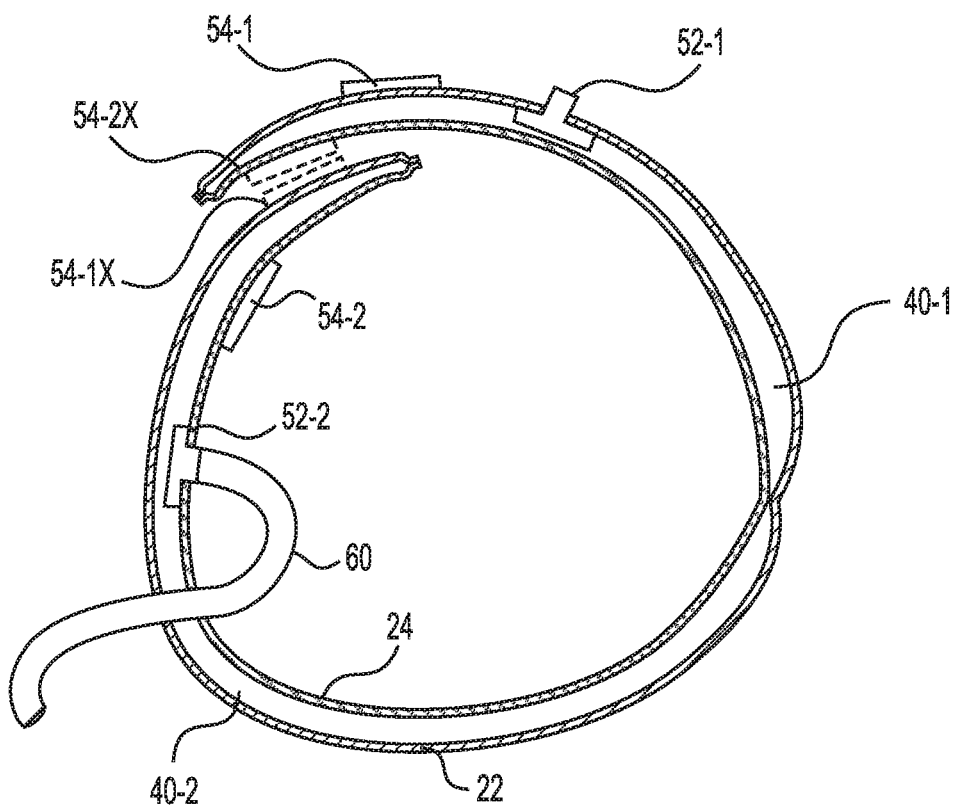
FIG. 9 is a view similar to that of FIG. 5 showing additional closure elements and illustrating a disadvantage of the additional closure elements.
Figure 10:
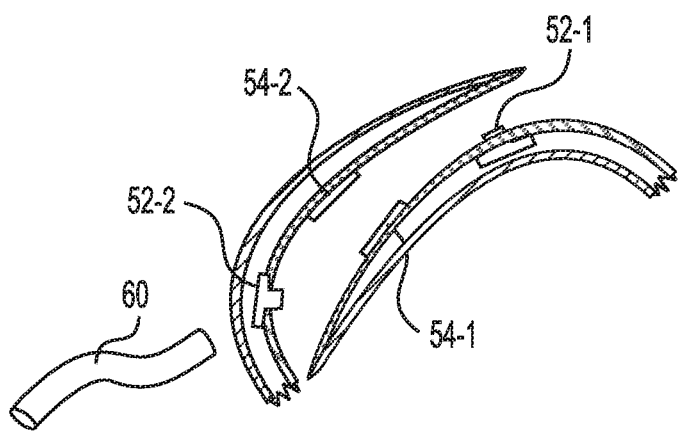
FIG. 10 is a view similar to that of FIG. 9 showing an advantage of the absence of the additional closure elements.

FIG. 9 shows another example of the undesirability of closure element 54-1X, 54-2X. The tube 60 can be connected to the second port 52-2, wherein the second port 52-2 may be used for a large patient. However, the cuff can be wrapped as in a configuration intended for a small patient (the second side 24 inward and the first side 22 outward). This incorrect wrapping is facilitated by the undesirable closure elements 54-1X, 54-2X. By contrast, as seen in FIG. 10, the absence of the "X" closure elements, and the presence of only the first closure element 54-1 and the second closure element 54-2 makes the error less likely.

Another advantage of the cuff is that a facility will be able to serve a wide range of patient sizes with fewer cuff sizes in its inventory, for example only two sizes instead of four sizes. Another advantage is that with fewer sizes required to serve the patient population, there is a diminished likelihood that the wrong size will be used. If a "one size fits all" or "one size fits almost all" cuff can be provided the required cuff inventory is further reduced, and the cuff will be appropriate for all patients with the possible exception of extremely large or small patients.

Figure 11:
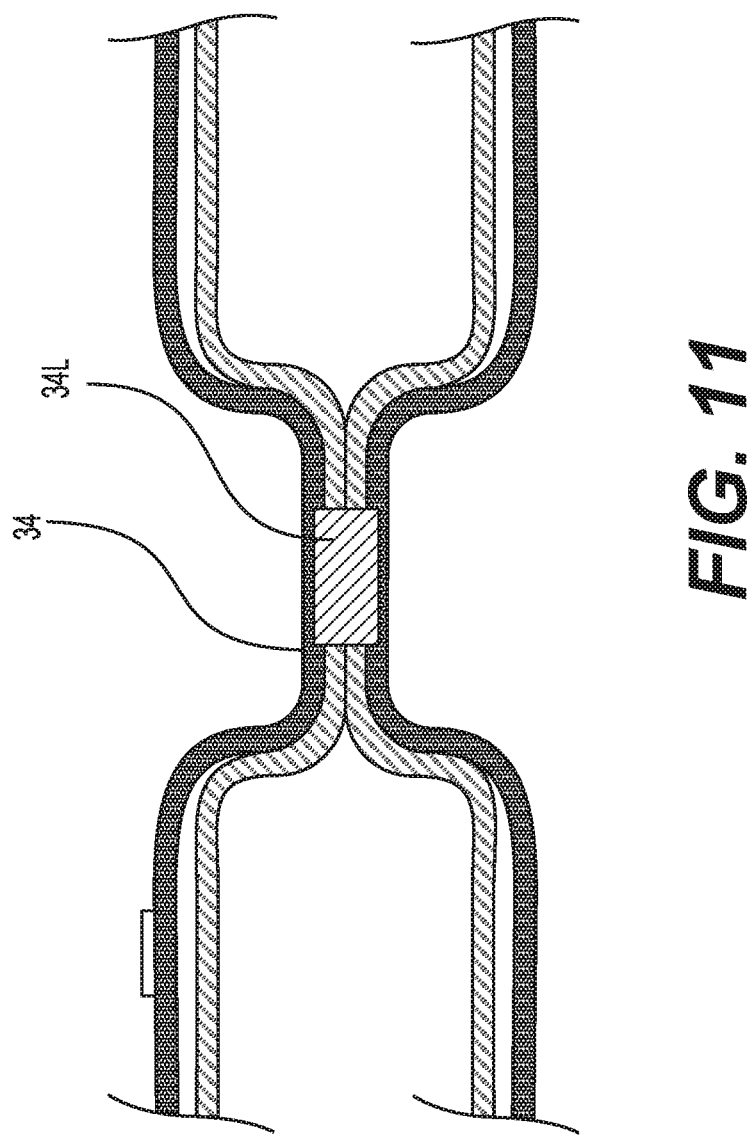
FIG. 11 is a longitudinally truncated view otherwise similar to that of FIG. 3 showing an alternative construction of the cuff.
Figure 12:
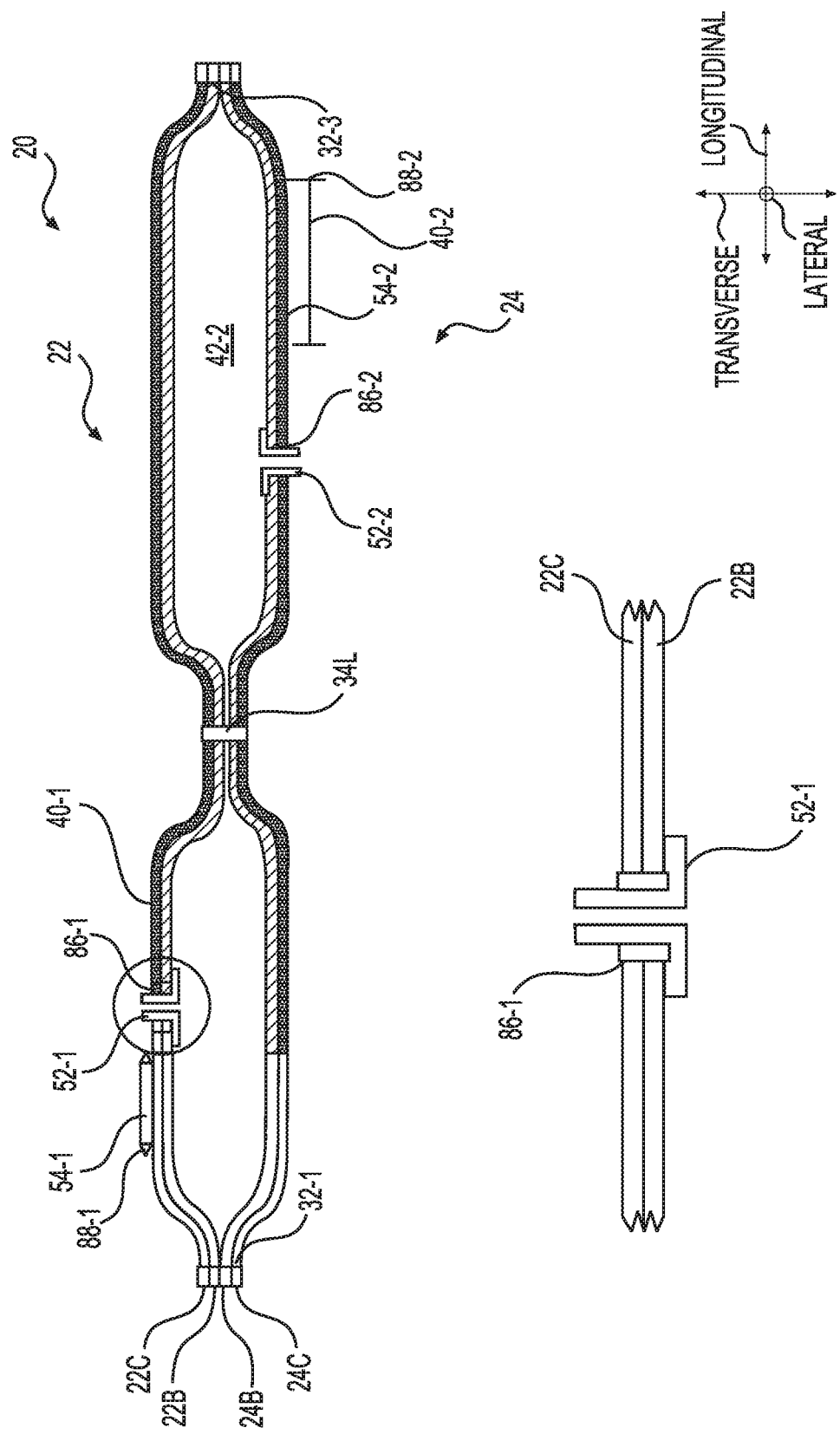
FIG. 12 is a view similar to that of FIG. 11 showing the entire longitudinal extent of the cuff.
Figure 13:
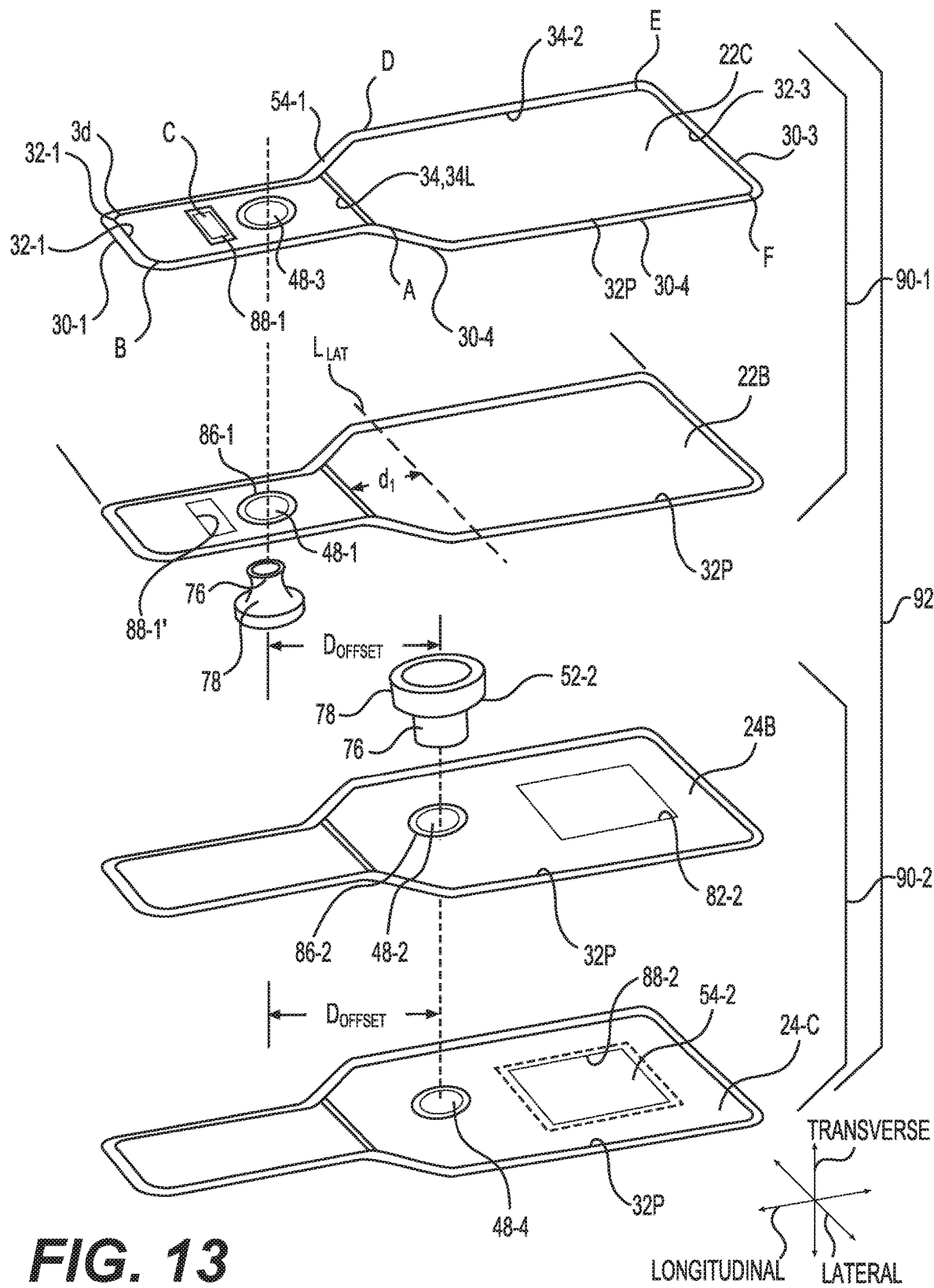
FIG. 13 is an exploded view of the cuff of FIG. 12 shown in connection with the description of a manufacturing technique.

FIGS. 11-13 show an alternative construction in which the second side 22 of the cuff is made of a first layer or sheet 22B of a first flexible material and a third layer or sheet 22C of a third material, and the second side 24 of the cuff is made of a second layer or sheet 24B of a second flexible material and a fourth layer or sheet 24C of a fourth material. The first sheet 22B and the second sheet 24B may be referred to as bladder sheets (hence the "B" suffix) because they bound the pressurizable cavities 42-1, 42-2 of the small patient bladder 40-1 and the large patient bladder 40-2. Additionally, the third sheet 22C and the fourth sheet 24C may be referred to as cover sheets (hence the "C" suffix) because they cover the bladder sheets.

When the cuff is in its finished form of FIG. 12, the first sheet 22B, the second sheet 24B, the third sheet 22C, and the fourth sheet 24C may be congruent. We use congruent in the conventional sense of being identical in form and coinciding exactly when superimposed as seen best in FIG. 13. In some additional embodiments, one or more of the first sheet 22B, the second sheet 24B, the third sheet 22C, and the fourth sheet 24C may be non-congruent. Each sheet, and therefore the cuff as a whole, may include a minor portion extending from nonperimetric terminus 34 to perimeter segment 30-1 (corresponding to the smaller patient bladder 40-1) and a major portion extending from nonperimetric terminus 34 to perimeter segment 30-3 (corresponding to the larger patient bladder 40-2). As seen best in FIG. 1, the minor portion of each sheet has a minor longitudinal dimension $D_{LONG,SM}$ and a minor lateral dimension $D_{LAT,SM}$. The major portion of each sheet has a major longitudinal dimension $D_{LONG,LG}$ and a major lateral dimension $D_{LAT,LG}$. In some embodiments, the major longitudinal dimension can be larger than the minor longitudinal dimension. In some additional embodiments, the major lateral dimension can be larger than the minor lateral dimension.

In some embodiments, a first port opening 48-1 can be configured to penetrate through first sheet 22B. Additionally, a second port opening 48-2 can be configured to penetrate through second sheet 24B. Further, a third port opening 48-3 can be configured to penetrate through third sheet 22C. Similarly, a fourth port opening 48-4 can be configured to penetrate through fourth sheet 24C. When the sheets are congruently arranged as in FIG. 13, the first port opening 48-1 and the second port opening 48-2 can be longitudinally offset from each other by an offset distance $D_{OFFSET}$ and the third port opening 48-3 and the fourth port opening 48-4 can be longitudinally offset from each other by the offset distance $D_{OFFSET}$. The port openings can be positioned on their respective sheets so that when the sheets are layered as they will be in the finished product and as suggested by FIG. 13, the first opening 48-1 and the third opening 48-3 may register with each other, the second opening 48-2 and the fourth opening 48-4 may register with each other, and the first opening 48-1 and the third opening 48-3 may be offset by $D_{OFFSET}$ from the second opening 48-2 and the fourth opening 48-4.

The first sheet 22B and the second sheet 24B may be respectively comprised of a first material and a second material that are weldable to themselves and to each other by heat welding or are joinable to themselves or each other by any other suitable technique. Suitable materials include polyethylene, polypropylene, and blends of polyethylene and polypropylene. The same material may be used for both sheets.

The third sheet 22C and the fourth sheet 24C may be respectively comprised of a third material and a fourth material that are not weldable to themselves or to each other, however a weld applied to the first sheet 22B and/or the second sheet 24B may penetrate through or into the material of the third sheet 22C and the fourth sheet 24C. The third material and the fourth material may both be the same material. One example material suitable for the third sheet 22C and the fourth sheet 24C is a paper-like material. One suitable paper-like material is comprised approximately of 40% to 70% paper pulp with the balance being polyethylene and/or polyester fibers. Another suitable paper-like material is comprised approximately of 50% to 60% paper pulp with the balance being polyethylene and/or polyester fibers. Another example of a suitable material is a creped spun lace material. One specific example of a creped spun lace material is Pro Towel, in particular Pro Towel 93141. (To Applicant's knowledge, the name Pro Towel need not be accompanied by a "TM" or ® symbol.)

In some embodiments, the use of polyethylene and/or polypropylene is advantageous due to their cost effectiveness relative to vinyl, their weldability, and the fact that they are nonporous and therefore capable of withstanding the pressurization required to take a blood pressure reading. However, polyethylene and polypropylene are weak in tension, and from that standpoint are not as desirable. The paper-like material, although porous and therefore not pressurizable, is strong in tension. The use of polyethylene or polypropylene to form the pressure containment bladder, in combination with the use of the paper-like material as a tension bearing covering, makes it possible to benefit from the advantages of each material and to use each material to negate the disadvantages of the other material.

A method of manufacturing the blood pressure cuff of FIGS. 11-13 includes the steps described below. As noted above, the first sheet 22B, the second sheet 24B, the third sheet 22C, and the fourth sheet 24C of the fully assembled finished product may be congruent. The manufacturing method will be described as if the provided sheets of material were congruent just as in the finished product and as seen in FIG. 13, and as if the dimensions of the provided sheets were the same as the dimensions of the finished product. However this is not a limitation of the manufacturing process. For example, referring to the generic illustration of FIG. 14, one or more of the provided sheets of material $S_{PROV}$ may be oversized relative to the finished planform $S_{FINISHED}$ of the cuff. At an appropriate point in the manufacture of the cuff, a trimming operation removes the excess material, which is the portion of $S_{PROV}$ not present in $S_{FINISHED}$. Accordingly, references to the perimeter in the descriptions of the manufacturing methods below mean the location of the perimeter of the finished cuff, not the perimeter of an oversized piece of material.

Figure 15:
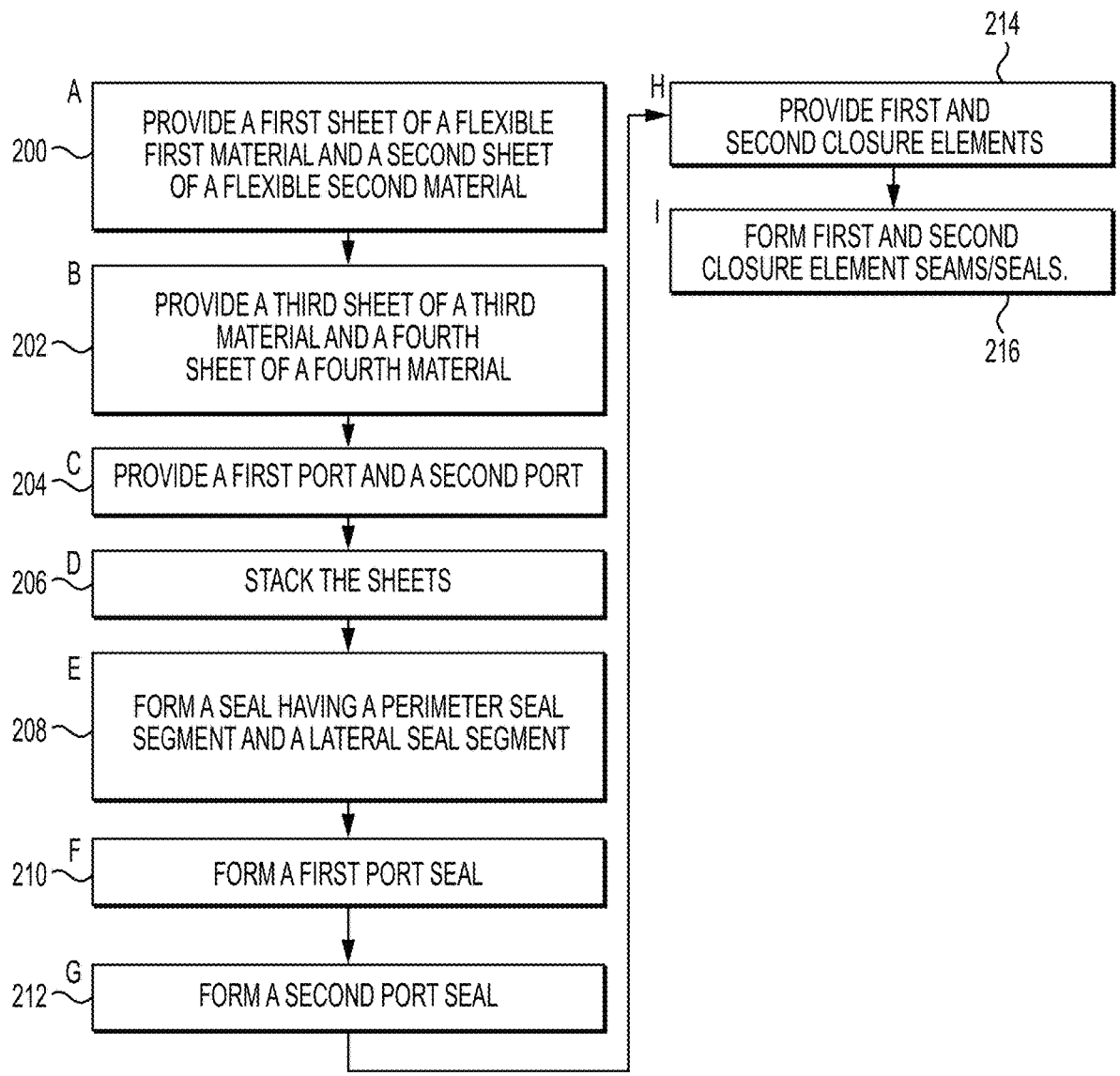
FIG. 15 is a block diagram of a method of manufacturing the cuff of FIGS. 11-13.

Referring additionally to FIG. 15 the steps of the method are:

A) (Block 200) Provide the first sheet 22B of a first flexible material having a first port opening 48-1 and a second sheet 24B of a second flexible material having a second port opening 48-2. The first sheet 22B and the second sheet 24B may be comprised of materials (e.g., the first flexible material and the second flexible material) that are weldable to each other. In some examples, the flexible first material and the flexible second material may be the same flexible material.

B) (Block 202) Provide a third sheet 22C of a third material having a third port opening 48-3, and a fourth sheet 24C of a fourth material having a fourth port opening 48-4. The materials of which the third sheet 22C and the fourth sheet 24C are made of need not be weldable to each other. In some examples, the third material and the fourth material may be the same material as each other.

C) (Block 204) Provide a first port 52-1 and a second port 52-2, each of which has a tube portion 76 and a flange portion 78.

D) (Block 206) Stack or layer the sheets so that:
  1) the first sheet 22B and the second sheet 24B are transversely adjacent to each other,
  2) the third sheet 22C is transversely adjacent to the first sheet 22B, and the third port opening 48-3 registers with the first port opening 48-1,
  3) the fourth sheet 24C is transversely adjacent to the second sheet 24B, and the second port opening 48-2 registers with the fourth port opening 48-4.

Figure 14:
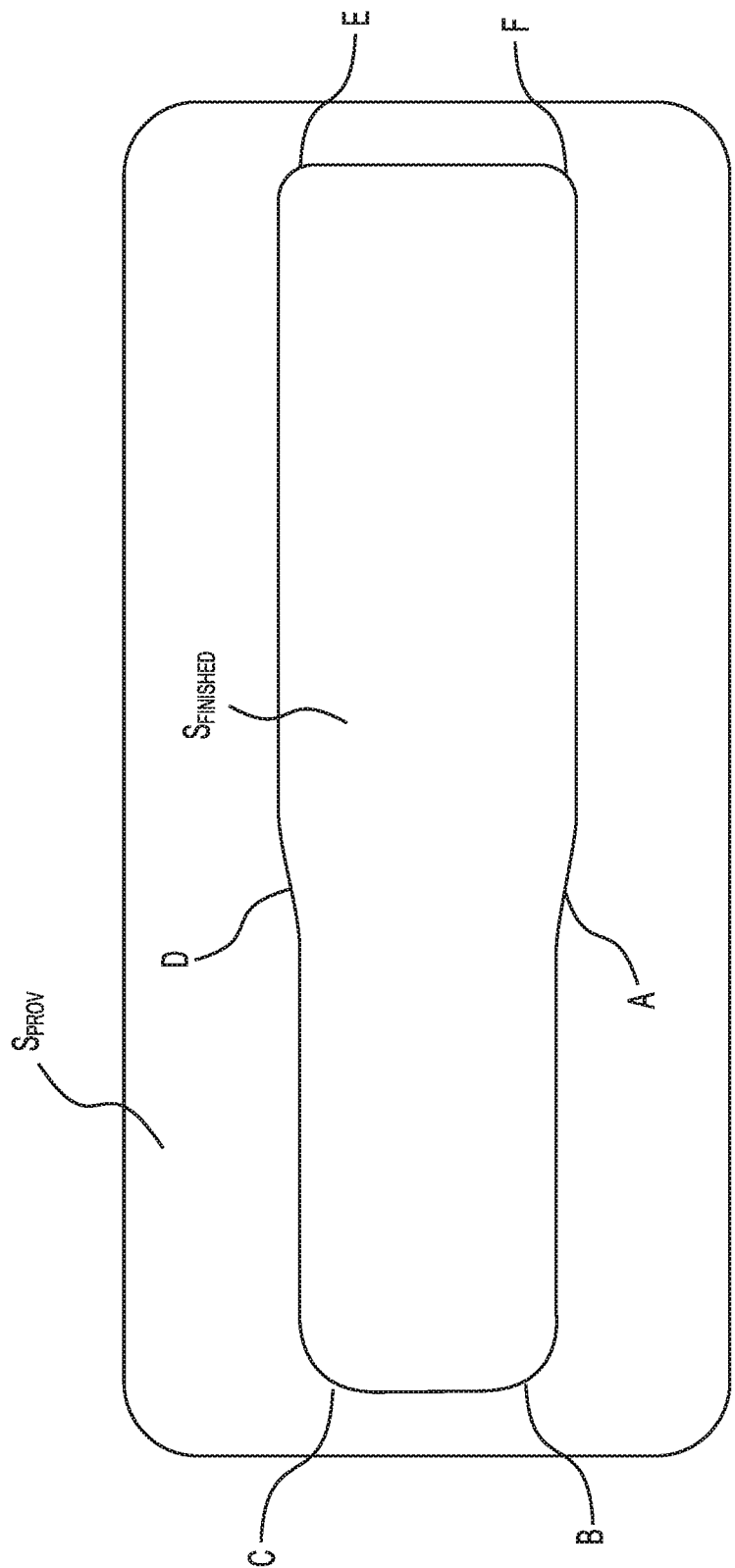
FIG. 14 is a plan view of a piece of material which is representative of any of the sheets of material of FIG. 13, and an outline of the planform of a finished cuff showing the possibility of manufacturing the cuff from a sheet or sheets of material that is/are oversized relative to the finished cuff and that is/are trimmed to the size of the finished cuff at an appropriate point in the manufacturing process.

E) (Block 208) Form a seal having a perimeter seal segment 32P and a nonperimetric lateral seal segment 34L. The perimeter seal segment 32P is the combination of seal segments 32-1, 32-2, 32-3, 32-4 of FIG. 1. Perimeter seal segment 32P may join the first sheet 22B, the second sheet 24B, the third sheet 22C, and the fourth sheet 24C to each other along their respective cuff perimeter segments. The joinder is described as being at the cuff perimeter (rather than at the perimeter of the provided sheet) to reflect the fact that if one or more of the provided sheets includes excess material as seen in FIG. 14, the perimeter of the provided sheet $S_{PROV}$ differs from the perimeter of the finished cuff $S_{FINISHED}$. Therefore, even if excess material is present, the perimeter seal segment is formed at the perimeter of $S_{FINISHED}$ not at the perimeter of $S_{PROV}$.

Referring momentarily again to FIG. 4, "perimeter" need not be at the actual edges of the cuff, but may be offset slightly from the actual edges by a small amount d. The nonperimetric lateral seal segment 34L cooperates with perimeter seal segment 32P to define a smaller patient bladder 40-1 and a larger patient bladder 40-2. The smaller patient bladder 40-1 may be bounded laterally and longitudinally by the lateral seal segment 34L and a minor portion of the perimeter seal segment which extends from A to B to C to D (labeled only on FIG. 13 at the third sheet 22C and on FIG. 14). The larger patient bladder 40-2 may be bounded laterally and longitudinally by the lateral seal and a major portion of the perimeter seal segment which extends from A to F to E to D (labeled only on FIG. 13 at the third sheet 22C and on FIG. 14). The smaller patient bladder 40-1 and the larger patient bladder 40-2 may be bounded transversely by respective portions of the first sheet 22B and the second sheet 24B.

F) (Block 210) Form a first port seal 86-1 joining the first port 52-1 to the first sheet 22B. The seal may be a heat weld. As seen best in the inset of FIG. 12, the heat weld for first port 52-1 extends transversely through third sheet 22C and first sheet 22B and circumferentially along flange 78 of port 52-1.

G) (Block 212) Form a second port seal 86-2 joining the second port 52-2 to the second sheet 24B. The seal may be a heat weld. The heat weld for second port 52-2 extends transversely through fourth sheet 24C and second sheet 24B and circumferentially along flange 78 of port 52-2.

The method of manufacture may also include the following steps:

H) (Block 214) Provide a first closure element 54-1 and a second closure element 54-2.

I) (Block 216) Form a first closure seam 88-1 joining first closure element 54-1 to the first side 22 of the cuff and form a second closure seam 88-2 joining second closure element 54-2 to the second side 24 of the cuff. The seams may be heat weld seals. The heat weld for first closure element 54-1 may extend transversely through the third sheet 22C and into the first sheet 22B along the four edges of the first closure element 54-1. Seal 88-1 is depicted on the third sheet 22C, and its outline 88-1' is depicted on the first sheet 22B. The heat weld for the second closure element 54-2 may extend transversely through the fourth sheet 24C and into the second sheet 24B along the four edges of closure element 54-2. Seal 88-2 is depicted on sheet 24C, and its outline 88-2' is depicted on sheet 24B.

Figure 16:
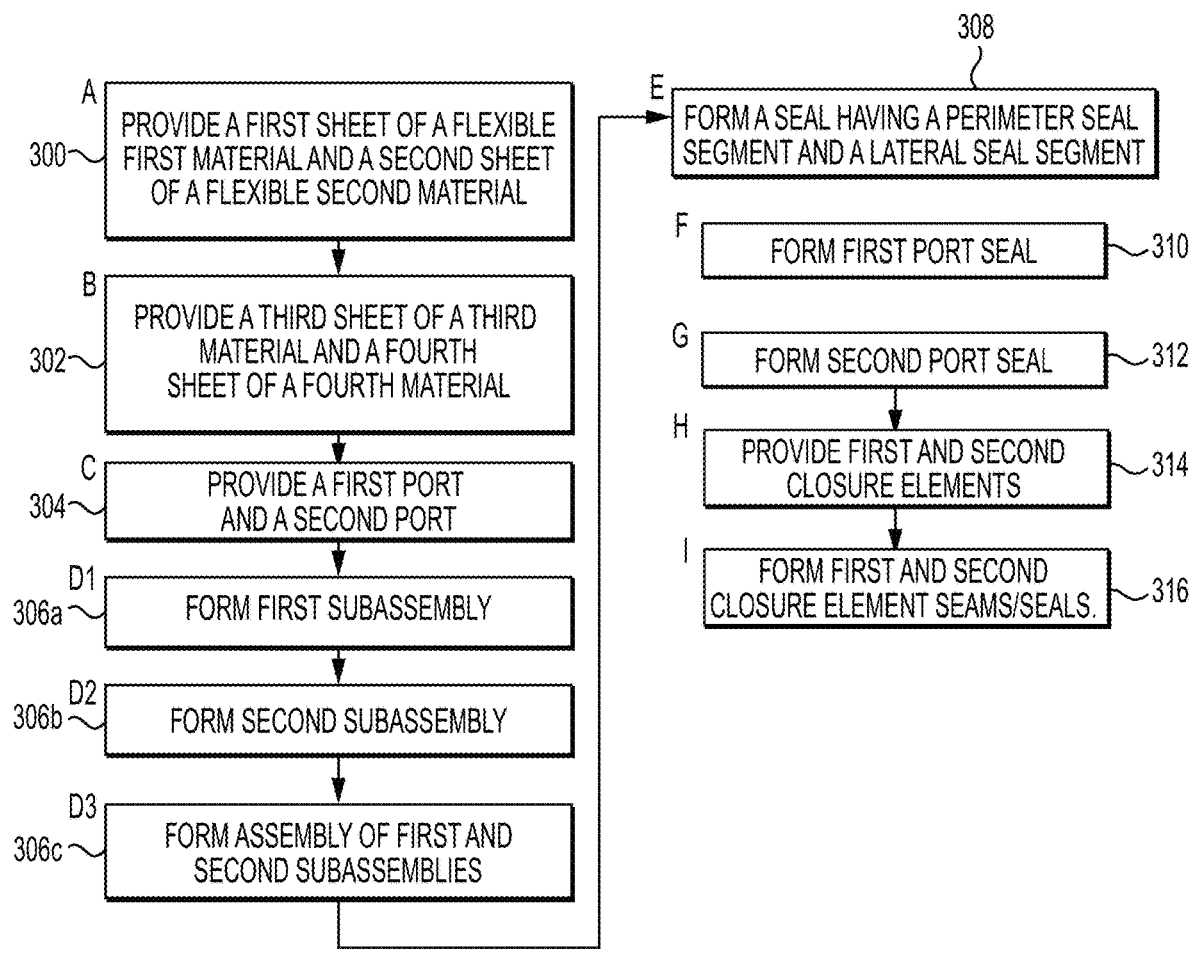
FIG. 16 is a block diagram of another method of manufacturing the cuff of FIGS. 11-13.

FIG. 16 shows another method of manufacture of the cuff of FIGS. 11-13. Blocks 300-304 (steps A, B, C) of FIG. 16 may be the same as blocks 200-204 (steps A, B, C) of FIG. 15. The foregoing description of steps A, B and C of FIG. 15 applies equally to steps A, B and C of FIG. 16.

The manufacturing method of FIG. 16 may further include the steps set forth below:

D1) (Block 306A) Form a first subassembly 90-1 of the first sheet 22B and the third sheet 22C, wherein the first sheet 22B and the third sheet 22C may be arranged so that first port opening 48-1 registers with third port opening 48-3 and so that the first port 52-1 projects through the registered first port opening 48-1 and third port opening 48-3.

D2) (Block 306B) Form a second subassembly 90-2 of the second sheet 24B and the fourth sheet 24C, wherein the second sheet 24B and the fourth sheet 24C may be arranged so that second port opening 48-2 registers with fourth port opening 48-4 and so that the second port 52-2 projects through the registered second port opening 48-2 and fourth port opening 48-4.

D3) (Block 306C) Form an assembly 92 of the first subassembly 90-1 and the second subassembly 90-2 arranged so that the first sheet 22B and the second sheet 24B are internal sheets, and the third sheet 22C and the fourth sheet 24C are external sheets.

The manufacturing method of FIG. 16 may further include the steps at blocks 308-316 (steps E through I) of FIG. 16, which may be the same as blocks 208-216 (steps E through I) of FIG. 15. The foregoing description of steps E through I of FIG. 15 can apply equally to steps E through I of FIG. 16.

In a variant example of the manufacturing method, the step D1 of forming the first subassembly 90-1 (block 306A) can include stabilizing the first subassembly 90-1 and/or the step D2 (block 306B) of forming the second subassembly 90-2 can include stabilizing the second subassembly 90-2. Stabilizing refers to making a connection which connects the sheets of the respective subassembly to each other (connecting the first sheet 22B to the third sheet 22C for the first subassembly 90-1; connecting the second sheet 24B to the fourth sheet 24C for the second subassembly 90-2). Stabilizing may also include connecting the first port 52-1 and the second port 52-2 to their respective subassemblies. Taking the first subassembly 90-1 as an example, the connection between the first sheet 22B and the third sheet 22C may be a heat welded connection between the first sheet 22B and the third sheet 22C and the connection for the first port 52-1 may be a heat welded connection. The connection between the first sheet 22B and the third sheet 22C may be present at the cuff perimeter, but need not be a continuous connection that extends along the entire perimeter. Likewise, the connection for the first port 52-2 need not extend completely around flange 78. Instead the connections may be a series of "spot" connections. The intent of the stabilization is to keep the components of each subassembly 90-1, 90-2 in their correct relationship to each other before and during formation of assembly 92 at step D3 (block 306C).

In some embodiments, a blood pressure cuff can comprise a first side and a second side opposite the first side. Additionally, the first side can be sealed to the second side at a cuff perimeter. The cuff perimeter may include a first perimeter segment that extends substantially perpendicular to a longitudinal axis, a second perimeter segment that extends substantially parallel to the longitudinal axis, a third perimeter segment extending substantially parallel to the first perimeter segment, and a fourth perimeter segment extending substantially parallel to the second perimeter segment. The longitudinal axis can be a central axis on the blood pressure cuff that extends along a length of the blood pressure cuff. Further, a first bladder of the blood pressure cuff can be partially defined by the first perimeter segment, the second perimeter segment, and the fourth perimeter segment and a second bladder of the blood pressure cuff can be at least partially defined by the third perimeter segment, the second perimeter segment, and the fourth perimeter segment. In some examples, the first bladder and the second bladder can be fluidly isolated from each other. A first port can be fluidly connected to the first bladder and extend outward from the first side of the cuff. A second port can be fluidly connected to the second bladder and extend outward from the second side of the cuff. A first closure assembly can be configured to secure the blood pressure cuff around a limb of a patient in a first sleeve configuration. Similarly, A second closure assembly can be configured to secure the blood pressure cuff around the limb in a second sleeve configuration. The first closure assembly can be located on the first side of the blood pressure cuff while the second closure assembly can be located on the second side of the blood pressure cuff.

In some examples of the blood pressure cuff the first bladder can be associated with a first width extending substantially parallel to at least a first portion of the first perimeter segment and a first length extending substantially parallel to a second portion of the second perimeter segment, and a first volume. Similarly, the second bladder can be associated with a second width extending substantially parallel to at least a third portion of the third perimeter segment, a second length extending substantially parallel to a fourth portion of the fourth perimeter segment, and a second volume. The first width can be less than the second width and the first volume can be less than the second volume. The first width, the second width, the first length, and the second length may be determined when the first bladder and/or the second bladder are uninflated.

In some additional examples, the first closure assembly can be a first closure element disposed on the first side of the blood pressure cuff between the first perimeter segment and the first port and can be configured to mate with a second closure element disposed on the second side of the cuff between the third perimeter segment and the second port. Additionally, the first port, the second port, the first closure element, and the second closure element can be configured so that when the cuff is in the first sleeve configuration the first port is exposed and extends radially outward from the first side for so that the first bladder is utilized for a blood pressure measurement and the second port is inaccessible during the blood pressure measurement. Further, the second port can be spaced from the limb of the patient by the first bladder of the blood pressure cuff during the blood pressure measurement. Similarly, the first closure element and the second closure element can be configured such that, when mated, the first closure element and the second closure element are spaced from the limb of the patient by at least the first bladder of the blood pressure cuff.

In some further examples, the blood pressure cuff can includes a first size marker on a first side of the first bladder, a first range guide on the first side of the second bladder, a second size marker on a second side of the second bladder, and a second range guide on the second side of the first bladder. The first size marker and the first range guide can be configured to indicate, when the blood pressure cuff is in the first sleeve configuration, whether the blood pressure cuff fits the patient. Similarly, the second size marker and the second range guide can be configured to indicate, when the blood pressure cuff is in the second sleeve configuration, whether the blood pressure cuff fits the patient.

In some embodiments, a blood pressure cuff may include a longitudinal axis that extends substantially centrally along a length of the blood pressure cuff. A first bladder of the blood pressure cuff may extend substantially parallel to the longitudinal axis from a first cuff perimeter segment to a lateral seal that extends substantially perpendicular to the longitudinal axis. Additionally, the first bladder may include a first side and a second side opposite the first side. A second bladder may extend substantially parallel to the longitudinal axis from a second cuff perimeter segment to the lateral seal, the second bladder having a third side adjacent to the second side of the first bladder, and a fourth side opposite the third side, the fourth side being disposed adjacent to the first side of the first bladder. In addition to the first bladder and the second bladder, the blood pressure cuff may include a first port that may be fluidly connected to the first bladder, the first port extending from the first side of the first bladder. Similarly, a second port may be fluidly connected to the second bladder, the second port extending from the third side of the second bladder. A first closure element can be located between the first perimeter segment and the first port and a second closure element can be located between the second perimeter segment and the second port. Further, the first bladder can be fluidly isolated from the second bladder.

In some examples, the first port, the second port, the first closure element, and the second closure element may be configured to maintain a sleeve configuration when placed on a limb of a patient for a blood pressure measurement. Additionally, the first port can be configured so that the first port is exposed on the first side of the first bladder. Accordingly, the first bladder can be inflated for a blood pressure measurement. Further, the second port can be inaccessible during the blood pressure measurement and radially separated from the limb of the patient by the first bladder. Similarly, the first closure element and the second closure element can be configured such that, when mated, the first closure element and the second closure element are spaced from a limb of a patient by at least the first bladder of the blood pressure cuff. The blood pressure cuff may include a first polarity indicator on the first side of the first bladder and a second polarity indicator on the third side of the second bladder.

In some embodiments, a blood pressure cuff may be manufactured by providing a first sheet of a first material, wherein the first sheet can be configured to include a first port opening and a first axis extending substantially centrally through the first port opening. Additionally, a second sheet of a second material may be provided, wherein the second sheet can be configured to include a second port opening and a second axis that extends substantially centrally through the second port opening. The first material may be weldable (e.g., heat weldable) to the second material. Further, a third sheet of a third material and a fourth sheet of a fourth material may be provided, wherein the third sheet can be configured to include a third port opening and a third axis extending substantially centrally through the third port opening and the fourth sheet can be configured to include a fourth port opening and a fourth axis extending substantially centrally through the fourth port opening. In some additional embodiments, a first port and a second port may be provided for the blood pressure cuff.

In some examples, the perimeter seal segment can be formed that seals the first sheet, the second sheet, the third sheet, and the fourth sheet together such that the first sheet is disposed adjacent to the second sheet, the third sheet is disposed adjacent to the first sheet, the first axis extends substantially collinear with the third axis, the second sheet is disposed adjacent to the fourth sheet, and the second axis extends substantially collinear with the fourth axis. Additionally, a lateral seal segment can be formed that defines a first bladder and a second bladder. The first bladder may be bounded laterally and longitudinally by the lateral seal segment and a first portion of the perimeter seal segment. Similarly, the second bladder may be bounded laterally and longitudinally by the lateral seal segment and a second portion of the perimeter seal segment. Further, a first port seal may be formed that seals the first port to the first sheet about a first perimeter of the first port, wherein at least part of the first port extending through the first port opening. Similarly, a second port seal may be formed that seals the second port to the second sheet about a second perimeter of the second port, wherein at least part of the second port extending through the second port opening.

In some additional examples, a first closure element and a second closure element may be provided for the blood pressure cuff. The first closure element can be affixed to the blood pressure cuff via a first closure seal that joins the first closure element to the third sheet opposite the first sheet. Similarly, the second closure element can be affixed to the blood pressure cuff via a second closure seal joining the second closure element to the fourth sheet opposite the second sheet. The first closure element may be affixed to the first surface of the third sheet and the second closure element may be affixed to the second surface of the fourth sheet.

In some further examples, forming the perimeter seal segment may be performed in a series of steps. For example, the first sheet and the third sheet may be sealed together so that the first port extends through the first port opening and the third port opening along the first axis and the third axis. Additionally, the second sheet and the fourth sheet may be sealed together so that the second port extends through the second port opening and the fourth port opening along the second axis and the fourth axis. Further, the first sheet and the second sheet may be sealed together to form a substantially fluid-tight bladder of the blood pressure cuff, wherein a first surface of the third sheet and a second surface of the fourth sheet form an outermost surface of the blood pressure cuff. Sealing the first sheet and the third sheet may include forming the first port seal that joins the first sheet and the third sheet to the first port along the first perimeter of the first port opening. Similarly, sealing the second sheet and the fourth sheet further may include forming the second port seal that joins the second sheet and the fourth sheet to the second port along the second perimeter of the second port opening.

Although this disclosure refers to specific embodiments, it will be understood by those skilled in the art that various changes in form and detail may be made without departing from the subject matter set forth in the accompanying claims.

We claim:

1. A blood pressure cuff, comprising:
   a first side;
   a second side opposite the first side, the first side being sealed to the second side at a cuff perimeter, the cuff perimeter comprising:
     a first perimeter segment that extends substantially perpendicular to a longitudinal axis, the longitudinal axis extending substantially centrally along a length of the blood pressure cuff,
     a second perimeter segment that extends substantially parallel to the longitudinal axis,
     a third perimeter segment extending substantially parallel to the first perimeter segment, and
     a fourth perimeter segment extending substantially parallel to the second perimeter segment;
   a first bladder of the blood pressure cuff, the first bladder at least partially defined by the first perimeter segment, the second perimeter segment, and the fourth perimeter segment;
   a second bladder of the blood pressure cuff, the second bladder is fluidly isolated from the first bladder and at least partially defined by the third perimeter segment, the second perimeter segment, and the fourth perimeter segment, wherein:
     the first perimeter segment at least partially defining the first bladder comprises a first free end of the cuff,
     the third perimeter segment at least partially defining the second bladder comprises a second free end of the cuff opposite the first free end,
   the second perimeter segment comprises a third free end of the cuff, and
   the fourth perimeter segment comprises a fourth free end of the cuff opposite the third free end;
   a first port fluidly connected to the first bladder, the first port extending outwardly from the first side of the cuff;
   a second port fluidly connected to the second bladder, the second port extending outwardly from the second side of the cuff;
   a first closure assembly disposed on the first side, the first closure assembly being configured to secure the blood pressure cuff around a limb of a patient in a first sleeve configuration; and
   a second closure assembly disposed on the second side, the second closure assembly being configured to secure the blood pressure cuff around the limb in a second sleeve configuration.

2. The blood pressure cuff of claim 1, wherein:
   the first bladder includes, when the first bladder is deflated, a first width extending substantially parallel to at least a first portion of the first perimeter segment, a first length extending substantially parallel to a second portion of the second perimeter segment, and a first volume;
   the second bladder includes, when the second bladder is deflated, a second width extending substantially parallel to at least a third portion of the third perimeter segment, a second length extending substantially parallel to a fourth portion of the fourth perimeter segment, and a second volume;
   the first width is less than the second width; and
   the first volume is less than the second volume.

3. The blood pressure cuff of claim 1, wherein:
   the first closure assembly is a first closure element disposed on the first side of the blood pressure cuff between the first perimeter segment and the first port;
   the first closure element is configured to mate with a second closure element disposed on the second side of the cuff between the third perimeter segment and the second port.

4. The blood pressure cuff of claim 1, wherein the cuff is reversible such that when the cuff is in the first sleeve configuration:
   the first side of the cuff is radially outward of the second side of the cuff,
   the first port is exposed and extends radially outward from the first side away from the longitudinal axis, and
   the second port extends radially inward from the second side toward the longitudinal axis; and when the cuff is in the second sleeve configuration:
   the second side of the cuff is radially outward of the first side of the cuff,
   the second port is exposed and extends radially outward from the second side away from the longitudinal axis, and
   the first port extends radially inward from the second side toward the longitudinal axis.

5. The blood pressure cuff of claim 1, wherein the first free end is separate from the second free end, and the third free end is separate from the fourth free end, the cuff further including a lateral seal extending from the third free end to the fourth free end.

6. The blood pressure cuff of claim 3, wherein the first closure element and the second closure element are configured such that, when mated, the first closure element and the second closure element are spaced from the limb of the patient by at least the first bladder of the blood pressure cuff.

7. The blood pressure cuff of claim 1, further comprising:
a first size marker on a first side of the first bladder;
a first range guide on the first side of the second bladder;
a second size marker on a second side of the second bladder; and
a second range guide on the second side of the first bladder;
wherein:
the first size marker and the first range guide are configured to indicate, when the blood pressure cuff is in the first sleeve configuration, whether the blood pressure cuff fits the patient; and
the second size marker and the second range guide are configured to indicate, when the blood pressure cuff is in the second sleeve configuration, whether the blood pressure cuff fits the patient.

8. A blood pressure cuff, comprising:
a longitudinal axis that extends substantially centrally along a length of the blood pressure cuff;
a first bladder extending along the longitudinal axis from a first cuff perimeter segment to a lateral seal that extends substantially perpendicular to the longitudinal axis, the first bladder having a first side and a second side opposite the first side;
a second bladder extending along the longitudinal axis from a second cuff perimeter segment to the lateral seal, the second bladder having a third side adjacent to the second side of the first bladder, and a fourth side opposite the third side, the fourth side being disposed adjacent to the first side of the first bladder;
a first port fluidly connected to the first bladder, the first port extending from the first side of the first bladder;
a second port fluidly connected to the second bladder, the second port extending from the third side of the second bladder;
a first closure element located between the first perimeter segment and the first port; and
a second closure element located between the second perimeter segment and the second port, wherein:
the cuff includes
a third cuff perimeter segment at least partially defining the first and second bladders,
a fourth cuff perimeter segment opposite the third cuff parameter segment, the fourth cuff parameter segment at least partially defining the first and second bladders,
the first cuff perimeter segment comprises a first free end of the cuff,
the second cuff perimeter segment comprises a second free end of the cuff opposite the first free end,
the third cuff perimeter segment comprises a third free end of the cuff,
the fourth cuff perimeter segment comprises a fourth free end of the cuff opposite the third free end, and
the first bladder is fluidly separate from the second bladder.

9. The blood pressure cuff of claim 8, wherein the first port, the second port, the first closure element, and the second closure element are configured so that, when the blood pressure cuff is in a sleeve configuration on a limb of a patient:
the first port is exposed on the first side of the first bladder, wherein the first bladder is inflatable for a blood pressure measurement; and
the second port is inaccessible.

10. The blood pressure cuff of claim 9, wherein the second port is radially separated from the limb of the patient by the first bladder.

11. The blood pressure cuff of claim 8, wherein the first closure element and the second closure element are configured such that, when mated, the first closure element and the second closure element are spaced from a limb of a patient by at least the first bladder of the blood pressure cuff.

12. The blood pressure cuff of claim 8 including:
a first size marker on the first side of the first bladder;
a first range guide on the fourth side of the second bladder;
a second size marker on the third side of the second bladder; and
a second range guide on the second side of the first bladder;
wherein:
the first size marker and the first range guide are configured to indicate, when the blood pressure cuff is in a first sleeve configuration, whether the blood pressure cuff fits a first patient; and
the second size marker and the second range guide are configured to indicate, when the blood pressure cuff is in a second sleeve configuration, whether the blood pressure cuff fits a second patient.

13. The blood pressure cuff of claim 8 including a first polarity indicator on the first side of the first bladder and a second polarity indicator on the third side of the second bladder.

14. The blood pressure cuff of claim 8, wherein:
the first bladder, when inflated, has a first volume;
the second bladder, when inflated, has a second volume; and
the first volume is less than the second volume.

15. A method of manufacturing a blood pressure cuff, comprising:
providing a first sheet of a first material, the first sheet having a first port opening, a first axis extending substantially centrally through the first port opening;
providing a second sheet of a second material, the second sheet having a second port opening, wherein a second axis extends substantially centrally through the second port opening, and the first material is weldable to the second material;
providing a third sheet of a third material, the third sheet having a third port opening, a third axis extending substantially centrally through the third port opening;
providing a fourth sheet of a fourth material, the fourth sheet having a fourth port opening, a fourth axis extending substantially centrally through the fourth port opening;
providing a first port and a second port;
forming a perimeter seal segment, the perimeter seal segment sealing the first sheet, the second sheet, the third sheet, and the fourth sheet together such that:
the first sheet is disposed adjacent to the second sheet,
the third sheet is disposed adjacent to the first sheet,
the first axis extends substantially collinear with the third axis,
the second sheet is disposed adjacent to the fourth sheet, and
the second axis extends substantially collinear with the fourth axis;

forming a lateral seal segment, the lateral seal segment that defines a first bladder and a second bladder, wherein:
- the first bladder is bounded laterally by the lateral seal segment and a first portion of the perimeter seal segment opposite the lateral seal segment,
- the second bladder is bounded laterally by the lateral seal segment and a second portion of the perimeter seal segment opposite the lateral seal segment, the first portion of the perimeter seal segment forming a first free end of the cuff, and the second portion of the perimeter seal segment forming a second free end of the cuff opposite and separate from the first free end,
- the first and second bladders are bounded longitudinally by a third portion of the perimeter seal segment and by a fourth portion of the perimeter seal segment opposite the third portion, the third portion forming a third free end of the cuff, and the fourth portion forming a fourth free end of the cuff opposite and separate from the third free end;

forming a first port seal, the first port seal sealing the first port to the first sheet about a first perimeter of the first port, at least part of the first port extending through the first port opening; and forming a second port seal, the second port seal sealing the second port to the second sheet about a second perimeter of the second port, at least part of the second port extending through the second port opening.

16. The method of claim 15 comprising:
providing a first closure element and a second closure element;
forming a first closure seal joining the first closure element to the third sheet opposite the first sheet; and
forming a second closure seal joining the second closure element to the fourth sheet opposite the second sheet.

17. The method of claim 15 wherein forming the perimeter seal segment further comprises:
- sealing the first sheet and the third sheet so that the first port extends through the first port opening and the third port opening along the first axis and the third axis;
- sealing the second sheet and the fourth sheet so that the second port extends through the second port opening and the fourth port opening along the second axis and the fourth axis;
- sealing the first sheet and the second sheet to form a substantially fluid-tight bladder of the blood pressure cuff, wherein a first surface of the third sheet and a second surface of the fourth sheet form an outermost surface of the blood pressure cuff.

18. The method of claim 17 wherein sealing the first sheet and the third sheet further comprises forming the first port seal joining the first sheet and the third sheet to the first port along the first perimeter of the first port opening.

19. The method of claim 17, wherein sealing the second sheet and the fourth sheet further comprises forming the second port seal joining the second sheet and the fourth sheet to the second port along the second perimeter of the second port opening.

20. The method of claim 17, further comprising:
providing a first closure element;
providing a second closure element;
affixing the first closure element to the first surface of the third sheet; and
affixing the second closure element to the second surface of the fourth sheet.

* * * * *